(12) United States Patent
Manfield

(10) Patent No.: US 12,079,462 B2
(45) Date of Patent: Sep. 3, 2024

(54) PARAMETERIZED SENSORY SYSTEM

(71) Applicant: Philip Manfield, Albany, CA (US)

(72) Inventor: Philip Manfield, Albany, CA (US)

(*) Notice: Subject to any disclaimer, the term of this patent is extended or adjusted under 35 U.S.C. 154(b) by 0 days.

(21) Appl. No.: 18/330,940

(22) Filed: Jun. 7, 2023

(65) Prior Publication Data

US 2023/0393724 A1 Dec. 7, 2023

Related U.S. Application Data

(63) Continuation of application No. 17/014,217, filed on Sep. 8, 2020, now Pat. No. 11,709,589, which is a continuation of application No. 15/974,015, filed on May 8, 2018, now Pat. No. 10,782,865.

(51) Int. Cl.

| | | |
|---|---|---|
| G06F 3/04847 | (2022.01) | |
| G06F 3/04817 | (2022.01) | |
| G08B 21/24 | (2006.01) | |
| G09B 19/00 | (2006.01) | |

(52) U.S. Cl.
CPC ...... *G06F 3/04847* (2013.01); *G06F 3/04817* (2013.01); *G08B 21/24* (2013.01); *G09B 19/00* (2013.01)

(58) Field of Classification Search
CPC . G06F 3/04847; G06F 3/04817; G08B 21/24; G09B 19/00
See application file for complete search history.

(56) References Cited

U.S. PATENT DOCUMENTS

| | | |
|---|---|---|
| 5,363,154 A | 11/1994 | Galanter et al. |
| 8,957,847 B1 | 2/2015 | Karakotsios et al. |
| 9,934,426 B2 | 4/2018 | Kim et al. |
| 2007/0166675 A1 | 7/2007 | Atkins et al. |
| 2011/0125844 A1 | 5/2011 | Collier et al. |
| 2012/0290950 A1 | 11/2012 | Rapaport et al. |
| 2013/0316324 A1 | 11/2013 | Hoffmann |
| 2013/0346515 A1 | 12/2013 | DeLuca et al. |
| 2014/0095189 A1 | 4/2014 | Holmes |
| 2014/0317522 A1 | 10/2014 | Lucero et al. |
| 2015/0104771 A1 | 4/2015 | Bernstein |
| 2015/0140527 A1 | 5/2015 | Gilad-Barach et al. |
| 2016/0117597 A1 | 4/2016 | Ono et al. |
| 2016/0155355 A1 | 6/2016 | Merzenich et al. |
| 2016/0379668 A1 | 12/2016 | Greig et al. |

(Continued)

*Primary Examiner* — Tadesse Hailu
(74) *Attorney, Agent, or Firm* — Young Basile Hanlon & MacFarlane, P.C.

(57) ABSTRACT

A processor is configured to execute instructions stored in a memory to control a traversal of a graphical element on a graphical user interface. While the graphical element is controlled to traverse the graphical user interface, the following are repeatedly performed. A random time at which a stimulus is to be output is obtained. A random duration associated with the stimulus is obtained. The stimulus is output for the user at the random time and for the random duration. The random duration is such that the output of the stimulus is outside a conscious awareness of the user. The output of the stimulus is configured to decrease a disturbance level associated with a disturbing memory of the user. A performance of a task related to the graphical element is monitored. After the repeated instruction, a score associated with the user is determined based on the performance of the task.

20 Claims, 5 Drawing Sheets

(56) References Cited

U.S. PATENT DOCUMENTS

| | | | |
|---|---|---|---|
| 2017/0150907 A1* | 6/2017 | Duffy | A61B 5/7435 |
| 2018/0055433 A1 | 3/2018 | Ally et al. | |
| 2018/0161626 A1 | 6/2018 | Fung | |
| 2018/0286272 A1 | 10/2018 | McDermott et al. | |
| 2019/0026679 A1 | 1/2019 | Pernot et al. | |
| 2019/0159716 A1 | 5/2019 | Alailima et al. | |
| 2019/0212815 A1* | 7/2019 | Zhang | G06V 10/82 |
| 2020/0297263 A1 | 9/2020 | Kouider et al. | |

* cited by examiner

PARAMETERIZED SENSORY SYSTEM

CROSS-REFERENCE TO RELATED APPLICATION(S)

This disclosure is a continuation of U.S. patent application Ser. No. 17/014,217, filed Sep. 8, 2020, which is a continuation of U.S. patent application Ser. No. 15/974,015, filed May 8, 2018, the entire disclosures of which are hereby incorporated by reference.

TECHNICAL FIELD

This disclosure relates to a parameterized sensory system.

BACKGROUND

Many non-computerized techniques have been developed to reduce the disturbance associated with memories of traumatic events. It is generally understood that, when unresolved, these events cause symptoms throughout life. In some cases, computerized techniques may be useful for reducing the disturbance associated with memories of traumatic events, but these typically require the assistance of a psychological professional.

SUMMARY

Disclosed herein are, inter alia, implementations of parameterized sensory systems and techniques.

In an implementation, an apparatus is provided. The apparatus includes an input interface, a memory, and a processor. The processor is configured to execute instructions stored in the memory to control a traversal of a graphical element on a graphical user interface. While the graphical element is controlled to traverse the graphical user interface, the processor is configured to repeatedly perform instructions to obtain a random time at which a stimulus is to be output; obtain a random duration associated with the stimulus; output, for a user, the stimulus at the random time and for the random duration, where the random duration is such that the output of the stimulus is outside a conscious awareness of the user, and where the output of the stimulus is configured to decrease a disturbance level associated with a disturbing memory of the user; and monitor a performance of a task related to the graphical element. After the repeated instructions, the processor is configured to execute instructions to determine a score associated with the user based on the performance of the task.

In an implementation, a system is provided. The system comprises a server device including a memory and a processor, in which the processor executes instructions stored in the memory. The instructions include instructions to control a traversal of a graphical element across a graphical user interface. While a graphical element is controlled to traverse the graphical user interface, the processor is configured to repeatedly execute instructions to obtain a random time at which a stimulus is to be output; obtain a random duration associated with the stimulus; output, for a user, the stimulus at the random time and for the random duration, where the random duration is less than a duration required by the user to process the stimulus, and where the output of the stimulus is configured to decrease a disturbance level associated with a disturbing memory of the user; and monitor a performance of a task related to the graphical element. After the repeated instructions, the processor is configured to execute instructions to determine a score associated with the user based on the performance of the task.

In an implementation, a method is provided. The method includes controlling a traversal of a graphical element across a graphical user interface. While the graphical element is controlled to traverse the graphical user interface, repeatedly performing obtaining a random time at which a stimulus is to be output; obtaining a random duration associated with the stimulus; outputting, for a user, the stimulus at the random time and for the random duration, where the random duration is less than a duration required by the user to process the stimulus; and monitoring a performance of a task related to the graphical element. The method further includes determining a score associated with the user based on the performance of the task.

BRIEF DESCRIPTION OF THE DRAWINGS

This disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
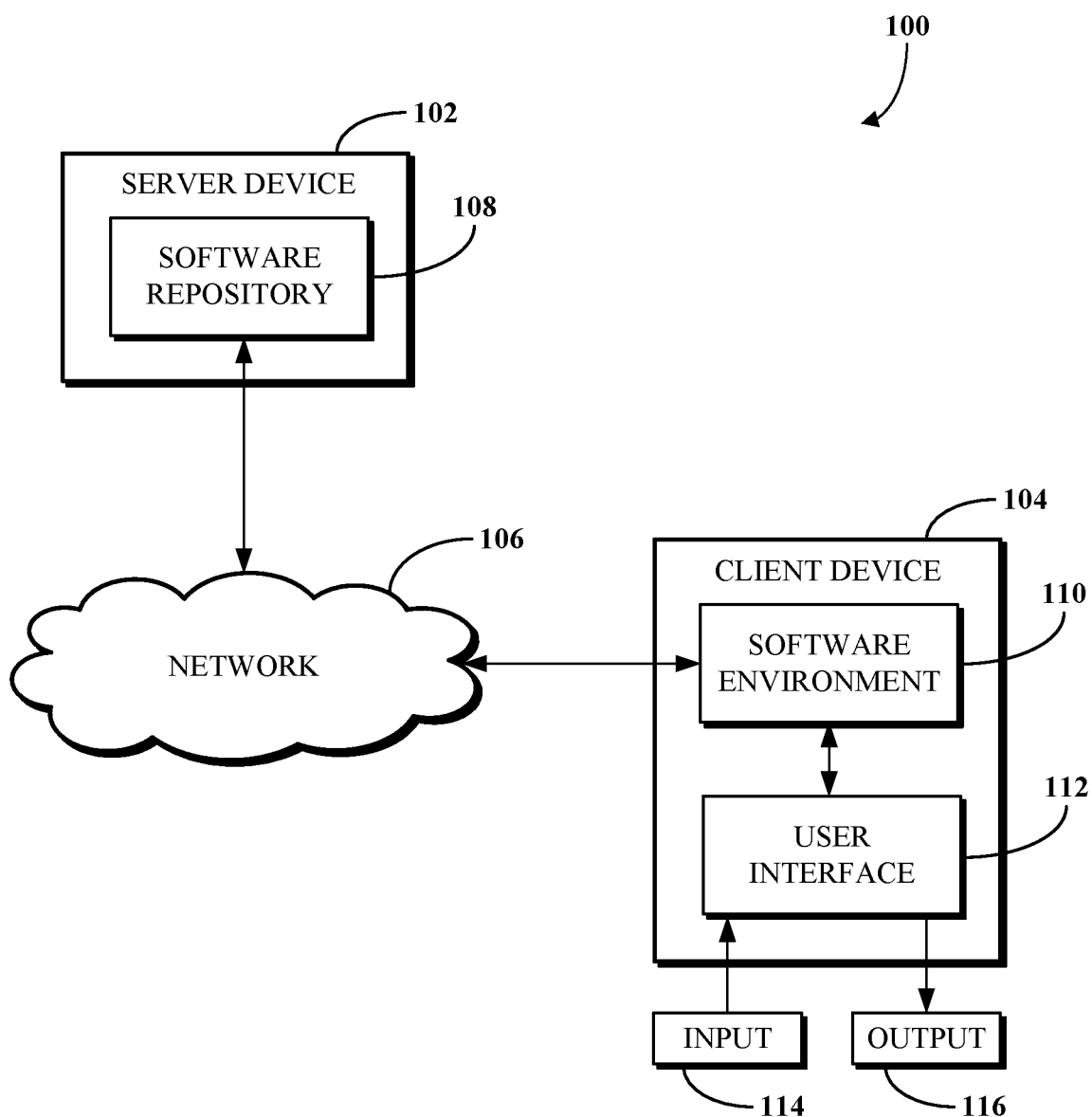
FIG. 1 is a block diagram of an example of a parameterized sensory system.

Common psychotherapeutic techniques for reducing disturbance levels associated with traumatic memories typically require the patient to think about the memory and become disturbed by it. However, this may cause the technique to fail because some patients may lack sufficient psychological stability to focus on such traumatic memories, and others may even refuse to participate in the therapeutic technique because they do not want to relive their disturbing memory. As such, the success rate for treating a disturbing memory using a typical psychotherapeutic technique may be reduced. Further, a variety of computer programs have been developed to mimic aspects of these techniques. However, they do not have a significant effect on the patient when used without the assistance of a psychological professional.

Implementations of this disclosure address problems such as these using systems and techniques that allow a user of a software program (e.g., a patient) to process a disturbing memory without consciously focusing on that disturbing memory. As a result, the user does not become disturbed by the thought of that memory. A psychotherapeutic technique performed using the systems and techniques of this disclosure includes asking the user to select a disturbing memory and then asking him or her to input a reminder phrase (e.g., a two word phrase) indicative or representative of the memory. The user is then asked to indicate a level of the disturbance on a value scale (e.g., 0 to 10, where 0 reflects that the memory is not disturbing to the user and 10 reflects that the memory is highly disturbing to the user).

The technique of this disclosure includes instructing the user to perform one or more tasks. Generally, a task for the user to perform during the exercise includes monitoring a visual stimulation element, which may, for example, be a graphical element that traverses locations of a display of a computing device used to implement the exercise. During the performance of those tasks, the reminder phrase input by the user is displayed for short periods of time at various locations about the display of the computing device. For example, the reminder phrase may appear to flash for a fraction of a second (e.g., generally, too short a period of time to be able to read the reminder phrase during operation) at randomized locations of the display. At times during the exercise (e.g., in the middle and at the end), the user is asked to indicate a new level of the disturbance on the value scale. The goal is for the new level of disturbance to be lower than the previous level of disturbance.

The exercise is not designed to cause the user to intentionally think about the selected memory. Rather, the user is cautioned to not deliberately think of the memory again after initially selecting it for the exercise. It is possible that thinking of the disturbing memory could prevent the exercise from being properly conducted. The inclusion of tasks for the user to perform during the exercise offers one mechanism for distracting the user from thinking about the disturbing memory. This exercise is thus designed to utilize non-conscious mechanisms embedded in the human system to achieve significant psychological impact (e.g., a reduction in the disturbance associated with a traumatic memory) without the assistance of a psychotherapy professional. One characteristic of this disclosure is thus that the systems and techniques described herein achieve stimulation outside the conscious awareness of the user by combining the brevity of the display of a message (e.g., the reminder phrase) with randomizing the location on a display at which the message appears, further while at the same time distracting the user with a task that requires full attention. This allows the software program to operate on the typical screen with a 60 mHz refresh rate and still achieve stimulation outside of the conscious awareness of the user.

The systems and techniques of this disclosure describe a software program for performing a psychotherapeutic technique. The implementations and examples of this software program provide targeted approaches to addressing psychotherapy-related concerns specific to a particular user who is using the software program. As such, the systems and techniques of this disclosure, including the execution of software programs associated therewith and results of such executions, are particular to the user of the software program.

To describe some implementations in greater detail, reference is first made to examples of hardware structures which may be used. FIG. 1 is a block diagram of an example of a parameterized sensory system 100. The parameterized sensory system 100 includes a server device 102 and a client device 104 that communicate over a network 106. Examples of devices used to implement the server device 102 and/or the client device 104 are described below with respect to FIG. 2. Examples of the network 106 may include a local area network, a wide area network, a machine-to-machine network, a virtual private network, or another public or private network.

The server device 102 transmits data associated with a software program for a psychotherapeutic technique to the client device 104 over the network 106. The server device 102 includes a software repository 108 used to store the data associated with the software program. For example, the data associated with the software program may include an executable software application file. In another example, the data associated with the software program may include one or more files that may be compiled (e.g., at a software environment 110 of the client device 104) to produce the software program. One or more versions of the software program may be stored in different stores of the software repository 108.

The client device 104 includes the software environment 110 and a user interface 112. The software environment 110 refers to or otherwise includes firmware and/or software used to execute the software program transmitted from the server device 102. For example, the software environment 110 can include an operating system, an application runtime environment, an application server (e.g., where the communications between the server device 102 and the client device 104 are over a virtualized network), an application programming interface, software libraries (e.g., code, script, or other data used to compile, prepare, or run the software program), or other data. The user interface 112 includes one or more input components and/or output components and software drivers for interfacing those input components and/or output components with the software environment 110. For example, the user interface 112 can include a keyboard for receiving input 114 and a display for displaying output 116.

The input 114 may be processed at the software environment 110, such as in connection with the execution of the software program. The input 114 and/or data associated with the execution of the software program may be transmitted from the client device 104 to the server device 102 over the network 106. For example, the server device 102 can store (e.g., within the software repository 108 or another data store aspect) the input 114, data indicative of the input 114, and/or the data associated with the execution of the software program. This stored data may be used, for example, to determine how to later update the software program.

Implementations of the parameterized sensory system 100 may differ from the examples described above with respect to FIG. 1. In some implementations, the parameterized sensory system 100 may omit the server device 102 and the network 106. For example, the software program used to perform the psychotherapeutic technique may be stored locally at the client device 104 (e.g., such as within a storage device or like component of the client device 104). The software environment 110 may thus execute the software program by loading the instructions or code for the software program from the storage device or like component into a memory of the client device 104. The input 114 and/or data associated with the execution of the software program may then be stored at the storage device or like component of the client device 104.

In some implementations, the client device 104 may be a virtual reality device or otherwise include a virtual reality aspect. For example, the client device 104 can include a virtual reality headset with a display. Information output for display at the client device 104 may thus be output for display at the virtual reality headset.

Figure 2:
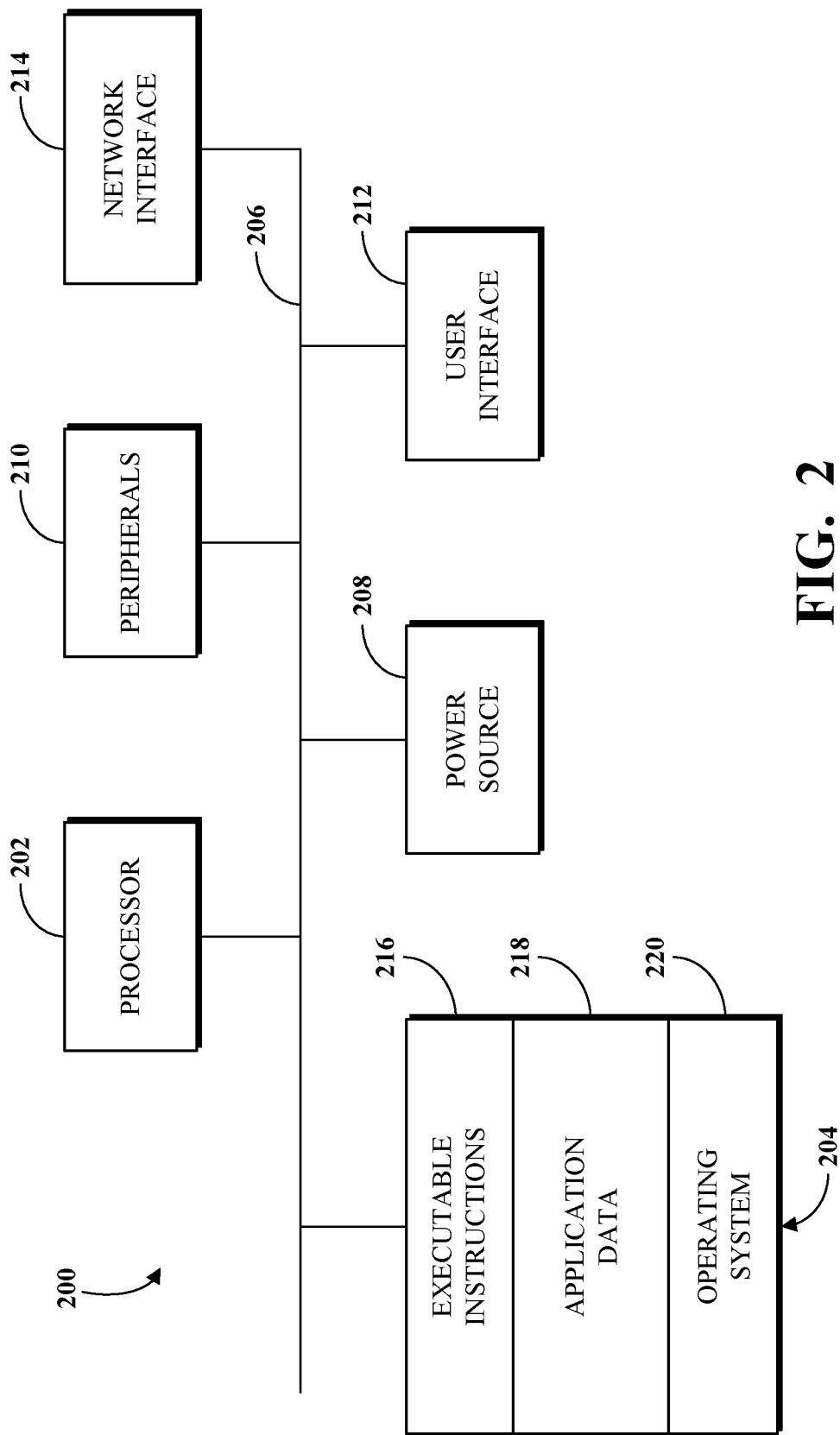
FIG. 2 is a block diagram of an example of an internal configuration of a computing device of a parameterized sensor system.

FIG. 2 is a block diagram of an example of an internal configuration of a computing device 200 of a parameterized sensory system, such as the parameterized sensory system 100 shown in FIG. 1. The computing device 200 may, for example, be the server device 102 or the client device 104 shown in FIG. 1. The computing device 200 includes components or units, such as a processor 202, a memory 204, a bus 206, a power source 208, peripherals 210, a user interface 212, and a network interface 214. One or more of the memory 204, the power source 208, the peripherals 210, the user interface 212, or the network interface 214 can communicate with the processor 202 via the bus 206.

The processor 202 is a central processing unit, such as a microprocessor, and can include single or multiple processors having single or multiple processing cores. Alternatively, the processor 202 can include another type of device, or multiple devices, now existing or hereafter developed, configured for manipulating or processing information. For example, the processor 202 can include multiple processors interconnected in any manner, including hardwired or networked, including wirelessly networked. For example, the operations of the processor 202 can be distributed across multiple devices or units that can be coupled directly or across a local area or other suitable type of network. The processor 202 can include a cache, or cache memory, for local storage of operating data or instructions.

The memory 204 includes one or more memory components, which may each be volatile memory or non-volatile memory. For example, the volatile memory of the memory 204 can be a DRAM module (e.g., DDR SDRAM) or another form of volatile memory. In another example, the non-volatile memory of the memory 204 can be a disk drive, a solid state drive, flash memory, phase-change memory, or another form of non-volatile memory configured for persistent electronic information storage. The memory 204 may also include other types of devices, now existing or hereafter developed, configured for storing data or instructions for processing by the processor 202.

The memory 204 can include data for immediate access by the processor 202. For example, the memory 204 can include executable instructions 216, application data 218, and an operating system 220. The executable instructions 216 can include one or more application programs, which can be loaded or copied, in whole or in part, from non-volatile memory to volatile memory to be executed by the processor 202. For example, the executable instructions 216 can include instructions for performing some or all of the techniques of this disclosure. The application data 218 can include user data, database data (e.g., database catalogs or dictionaries), or the like. The operating system 220 can be, for example, Microsoft Windows®, Mac OS X®, or Linux®, an operating system for a small device, such as a smartphone or tablet device; or an operating system for a large device, such as a mainframe computer.

The power source 208 includes a source for providing power to the computing device 200. For example, the power source 208 can be an interface to an external power distribution system. In another example, the power source 208 can be a battery, such as where the computing device 200 is a mobile device or is otherwise configured to operate independently of an external power distribution system.

The peripherals 210 includes one or more sensors, detectors, or other devices configured for monitoring the computing device 200 or the environment around the computing device 200. For example, the peripherals 210 can include a geolocation component, such as a global positioning system location unit. In another example, the peripherals can include a temperature sensor for measuring temperatures of components of the computing device 200, such as the processor 202.

The user interface 212 includes one or more input interfaces and/or output interfaces. An input interface may, for example, be a positional input device, such as a mouse, touchpad, touchscreen, or the like; a keyboard; or another suitable human or machine interface device. An output interface may, for example, be a display, such as a liquid crystal display, a cathode-ray tube, a light emitting diode display, or other suitable display.

The network interface 214 provides a connection or link to a network, for example, a local area network, a wide area network, a machine-to-machine network, a virtual private network, or another public or private network. The network interface 214 can be a wired network interface or a wireless network interface. The computing device 200 can communicate with other devices via the network interface 214 using one or more network protocols, such as using Ethernet, TCP, IP, power line communication, Wi-Fi, Bluetooth®, infrared, GPRS, GSM, CDMA, other protocols, or a combination thereof.

Implementations of the computing device 200 may differ from the examples described above with respect to FIG. 2. In some implementations, the computing device 200 can omit the peripherals 210. In some implementations, the memory 204 can be distributed across multiple devices. For example, the memory 204 can include network-based memory or memory in multiple clients or servers performing the operations of those multiple devices. In some implementations, the application data 218 can include functional programs, such as a web browser, a web server, a database server, another program, or a combination thereof.

Figure 3:
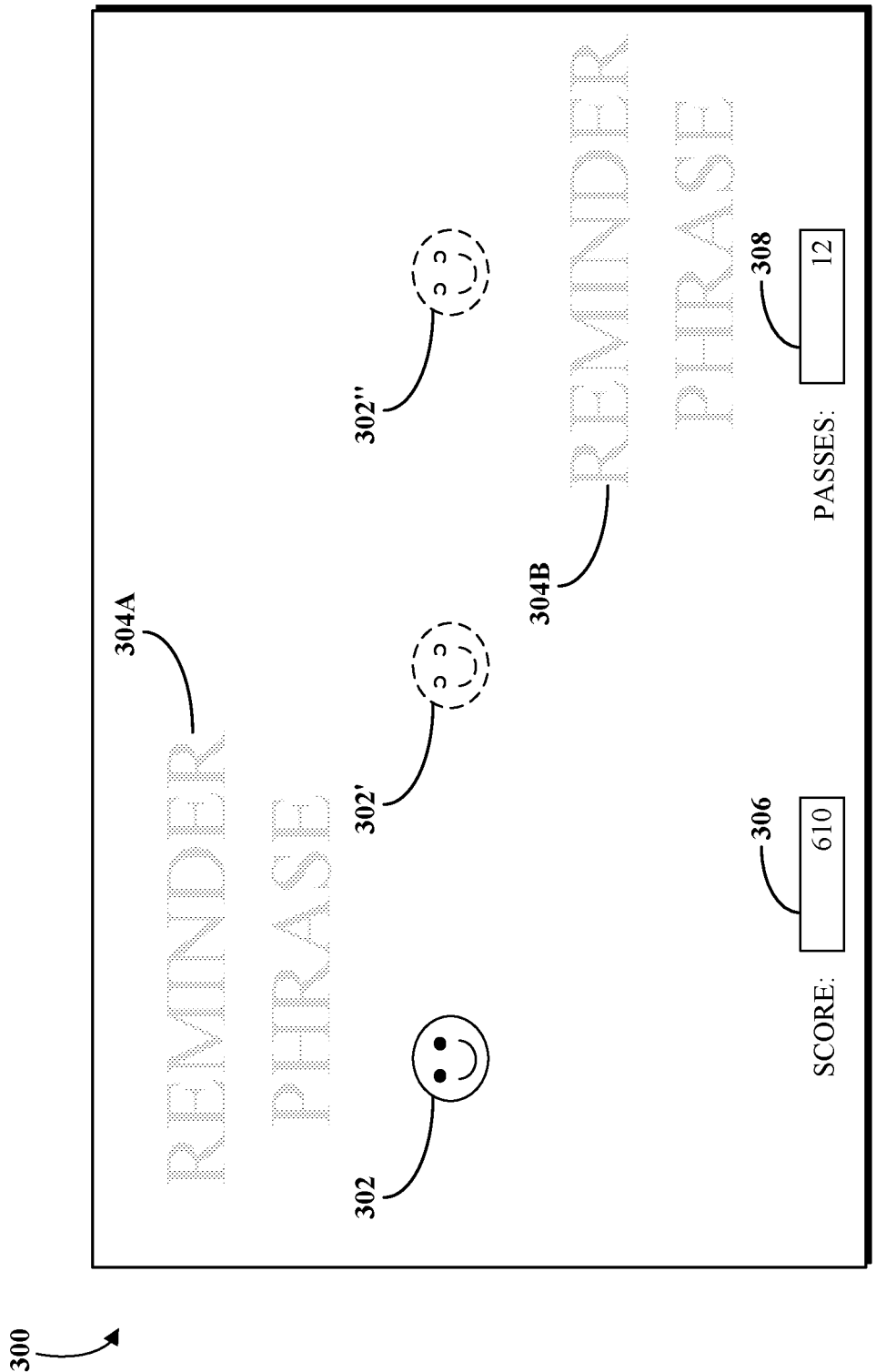
FIG. 3 is an illustration of an example of a GUI of a parameterized sensory system.

FIG. 3 is an illustration of an example of a GUI 300 of a parameterized sensory system, such as the parameterized sensory system 100 shown in FIG. 1. The GUI 300 may, for example, represent a GUI generated and output for display as part of a software program used to perform a psychotherapeutic technique. As such, the GUI 300 reflects information ultimately destined for display on a hardware device, such as the client device 104 shown in FIG. 1.

For example, the data can contain rendering instructions for bounded graphical display regions, such as windows, or pixel information representative of controls, such as buttons and drop-down menus. The rendering instructions can, for example, be in the form of HTML, SGML, JavaScript, Jelly, AngularJS, or other text or binary instructions for generating a graphical user interface on a display that can be used to generate pixel information. A structured data output of one device can be provided to an input of the hardware display so that the elements provided on the hardware display screen represent the underlying structure of the output data.

The GUI 300 includes a graphical element 302. The visual representation of the graphical element 302 as shown in the GUI 300 by example is of a smiley face. However, the graphical element 302 may have other visual representations. Further, the graphical element 302 may change visual representations during the operation of the GUI 300, such as from a first visual representation (e.g., the smiley face) to a second visual representation (e.g., an X or other symbol or icon). The graphical element 302 may be controlled to traverse across locations of the GUI 300. For example, the graphical element 302 may horizontally, vertically, or diagonally traverse the GUI 300. In another example, the graphical element 302 may traverse the GUI 300 in circular or other defined or undefined (e.g., randomized) directions.

The traversal of the graphical element as shown in the GUI 300 by example is a horizontal traversal in which the graphical element 302 moves from its initial location to a next location 302' and a final location 302". After arriving at a final location, (e.g., the final location 302"), the graphical element 302 can reverse traversal direction, such as to cause the graphical element 302 to return to its initial location. Alternatively, after arriving at the final location, the graphical element 302 can begin traversing the GUI 300 in a different manner or cease movement altogether.

The GUI 300 may at times include a reminder phrase 304A or 304B displayed at some location of the GUI 300. The reminder phrase 304A or 304B represents a parameter received as input, such as from a user of a software program associated with the GUI 300. The GUI 300 may display a single one of the reminder phrases 304A and 304B at a given time. Alternatively, multiple ones of the reminder phrases 304A and 304B may be displayed at once.

The location of the GUI 300 at which the reminder phrase 304A or 304B is displayed may be randomized. For example, the software program associated with the GUI 300 may include instructions for selecting a random location of the GUI 300 to display the reminder phrase 304A or 304B, such as according to a defined list of possible locations for the reminder phrase 304A or 304B. Alternatively, the location of the GUI 300 at which the reminder phrase 304A or 304B is displayed may be defined.

The user may perform a task based on movements of or other changes to the graphical element 302 during the operation of the GUI 300. For example, functionality of the software program associated with the GUI 300 may include determining whether a user of the software program has performed a task involving the graphical element 302. The task may include the user interacting with an input interface (e.g., a keyboard or a particular element thereof, such as a space bar or other key) of a computing device used to run the software program. For example, the task may include asking the user to press the space bar whenever the visual representation of the graphical element 302 changes.

The user may be scored based on his or her performance of the tasks. For example, where the task is for the user to interact with the computing device each time the user notices a change to the visual representation of the graphical element 302, the user may be scored for each such change based on the time that elapses between when the change occurs and when the user interacts with it. In another example, the user may be scored based on the number of times that he or she correctly interacted with the computing device responsive to a change to the visual representation of the graphical element 302. The element 306 represents a box including a score for the user based on his or her performance of the tasks. The element 308 represents a box including a number of times that the graphical element 302 has traversed across the GUI 300.

Implementations of the GUI 300 may differ from the examples described above with respect to FIG. 3. In some implementations, the GUI 300 can represent a GUI of a virtual reality system, such as a GUI output for display at a virtual reality headset or like device. For example, user interaction with the computing device can be using a physical controller of the virtual reality headset or like device. In another example, the user interaction can be using software of the virtual reality headset or like device, such as based on the direction the user views the displayed information.

In some implementations, the reminder phrase 304A, 304B may be an element other than text. For example, the reminder phrase 304A, 304B may be an image, a symbol, a collection of images and/or symbols, or some other digitally represented element or elements. In some implementations, the reminder phrase 304A, 304B may be represented other than using a visual stimulus. For example, the reminder phrase 304A, 304B may be an audial stimulus, such as may be included in an audio signal accompanying the GUI 300.

In some implementations, the GUI 300 may include other elements not shown. For example, the GUI 300 may include a pause element that, when interacted with by the user of the software program, causes the software program to pause running. In another example, the GUI 300 may include directions (e.g., text) for performing the tasks. In some implementations, the directions for performing the tasks may be included in a GUI that is output for display before the GUI 300, such as within a GUI sequence of the software program.

For example, the GUI sequence of the software program can include a first GUI that asks for a reminder phrase (e.g., output as the reminder phrase 304A or 304B), a second GUI that asks for an initial rating for a disturbance level associated with information (e.g., represented by the reminder phrase, as described below with respect to FIGS. 4 and 5), a third GUI that includes the directions for performing the tasks, a fourth GUI that is the GUI 300, a fifth GUI that asks for a new rating for the disturbance level, a sixth GUI that is a repeat of the GUI 300, and a seventh GUI that asks for a further new rating. In some implementations, these seven GUIs may be differently arranged.

To further describe some implementations in greater detail, reference is next made to examples of techniques used by systems, which may, for example, represent functionality of software programs used to perform psychotherapeutic techniques. The techniques described herein can be executed using computing devices, such as included within or otherwise using the systems, mechanisms, and devices described with respect to FIGS. 1 and 2. The techniques described herein can be performed, for example, by executing a machine-readable program or other computer-executable instructions, such as routines, instructions, or programs described according to Java, JavaScript, C++, Visual Basic, QBasic, or other such routines or instructions. The steps, or operations, of the techniques described herein or any other technique, method, process, or algorithm described in connection with the implementations disclosed herein can be implemented directly in hardware, firmware, software executed by hardware, circuitry, or a combination thereof.

Although the techniques described herein are each shown as a series of operations for clarity, implementations of those techniques or any other method, technique, process, and/or algorithm described in connection with the implementations disclosed herein can be performed in various orders and/or concurrently. Additionally, operations in accordance with this disclosure can be performed with other operations not presented and described herein. Furthermore, one or more aspects of the systems and techniques described herein can be omitted.

Figure 4:
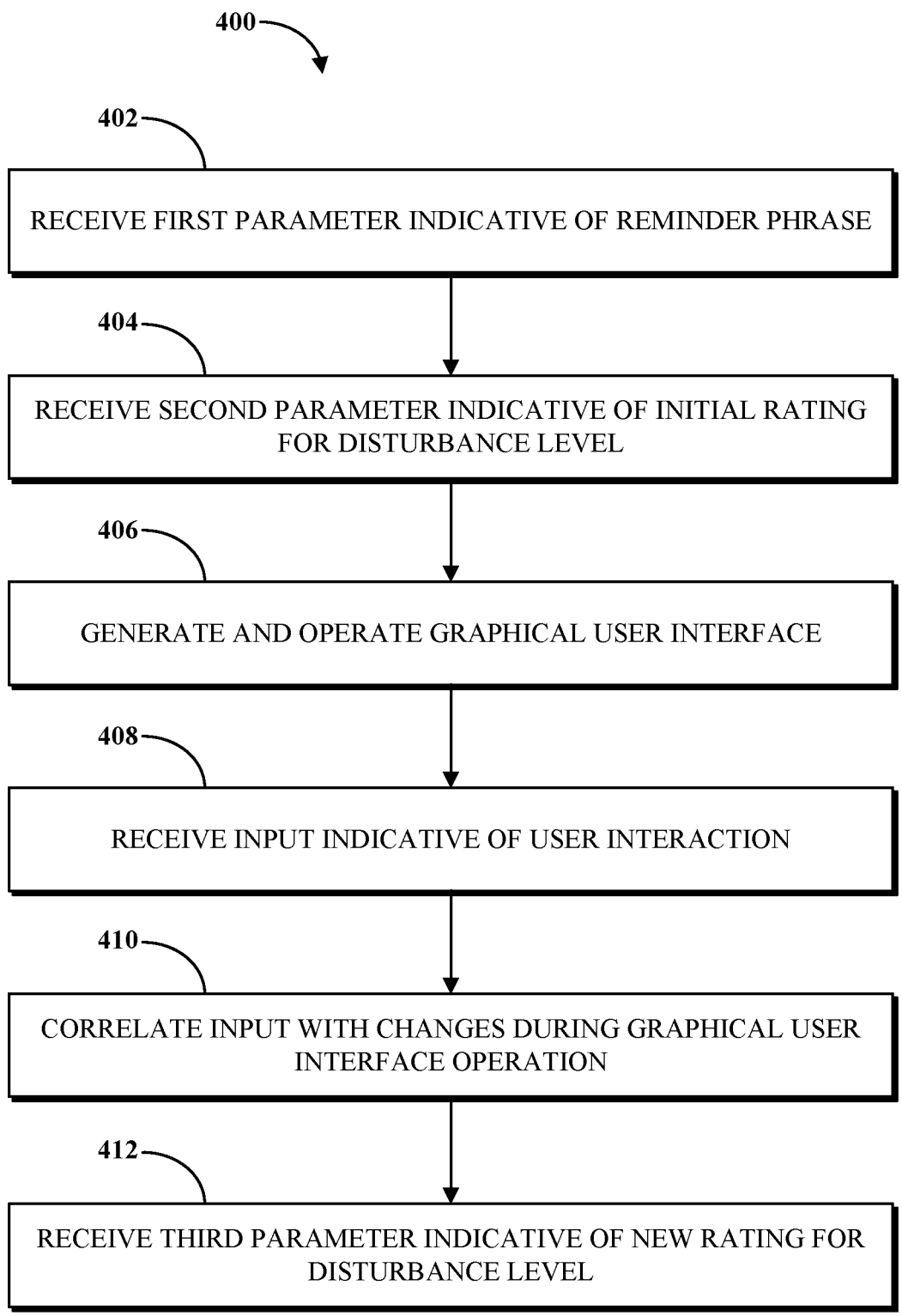
FIG. 4 is a flowchart illustrating an example of a technique for using interactions with a GUI to reduce a disturbance level associated with information particular to a user.

FIG. 4 is a flowchart illustrating an example of a technique 400 for using interactions with a GUI to reduce a disturbance level associated with information particular to a user. At 402, a first parameter is received. The first parameter is indicative of a reminder phrase. The reminder phrase is related to information particular to a user of a software program performing some or all of the operations of the technique 400. The reminder phrase is an N (e.g., two) word phrase intended to reflect or otherwise represent information, such as a disturbing memory of the user. The user may be directed to not consciously think about or otherwise recall the reminder phrase or the information to which the reminder phrase is related during the rest of the performance of the technique 400.

At 404, a second parameter is received. The second parameter is indicative of an initial rating for a disturbance level associated with the information. The disturbance level reflects a significance of the information to the user of the software program. The initial rating indicates how significant the information is to that user at the time the second parameter is received. For example, the initial rating may reflect a number on a valued scale, such as from one to ten, where one indicates that the information is least significant (e.g., that a disturbing memory is not very disturbing) and ten indicates that the information is most significant (e.g., that the disturbing memory is highly disturbing).

At 406, a GUI (e.g., the GUI 300 shown in FIG. 3) is generated and operated. The GUI is output for display, such as at a computing device running a software program that performs some or all of the operations of the technique 400. The GUI includes one or more elements which may be monitored or interacted with by a user of the software program, including the reminder phrase associated with the first parameter and a graphical element. That is, the software program may be run to measure or otherwise identify user interactions based on those one or more elements of the GUI. Implementations and examples for operating a GUI are described below with respect to FIG. 5.

At 408, input indicative of user interaction based on the elements of the GUI is received. The user interaction can refer to a user interacting with an input interface of the computing device used to run the software program. For example, the input interface can be a keyboard or a key thereof. The input includes data indicating that the input interface was interacted with, such as by the space bar of the keyboard having been pressed by the user.

At 410, the input is correlated with changes during the operation of the GUI. That is, the input may be received responsive to or in connection with a change in an element of the GUI during the operation of the GUI. For example, a visual representation of a graphical element of the GUI may change from a first visual representation to a second visual representation. The input indicative of the user interaction may be received responsive to that change. The input may then be correlated with that change.

Correlating the input with the changes during the operation of the GUI can include scoring the input based on a time interval between a first time at which the graphical element is changed and a second time at which the input is received. For example, the GUI can include an element reflect the score of a user of the software program. The score may increase during the operation of the GUI, such as based on the correlations between changes to the graphical element and input received based on user interactions with the input interface.

At 412, a third parameter is received. The third parameter is indicative of a new rating for a disturbance level associated with the information. The new rating reflects the significance of the information to the user at some time during or after the operation of the GUI. The user interaction with the input interface during the operation of the GUI causes a reduction to the disturbance level. As such, the new rating is lower than the initial rating. The third parameter thus reflects, such as of an output of the technique 400, a transformation of input received earlier in the performance of the technique 400 (e.g., the second parameter).

The user interaction with the input interface is without active processing (e.g., conscious thought) by the user as to the reminder phrase or the information (e.g., the disturbing memory). The cause of the reduction to the disturbance level during the operation of the graphical user interface is therefore related to the user interaction with the input interface without the active processing. Furthermore, given that the information is particular to the user, the outputting of the reminder phrase to the display over time during the operation of the GUI does not cause a reduction to a disturbance level associated with other information for another user.

In some implementations, the technique 400 includes outputting directions for interacting with the GUI to a display of the computing device prior to the operation of the GUI. For example, the directions may include directions for the user to interact with the input interface upon identifying a change to the graphical element.

In some implementations, the technique 400 includes further operations for receiving further input and further parameters indicative of ratings of the disturbance level. For example, the technique 400 may include, subsequent to receipt of the third parameter, further operate the GUI, and receiving further input indicative of further user interaction with the input interface by the user during the further operation of the GUI. A fourth parameter indicative of a further new rating for the disturbance level may then be received. The user interaction with the input interface during the further operation of the GUI may cause a further reduction to the disturbance level such that the further new rating is lower than the new rating. Although a third parameter is described, the technique 400 may include operations for receiving fourth parameters, fifth parameters, or otherwise Nth parameters for indicating new ratings for the disturbance level during the operation of the software program.

In some implementations, the technique 400 includes using machine learning functionality to store data indicative of the parameters and/or of the user interaction with software performing the technique 400. For example, the machine learning functionality can monitor input received from the user, such as with respect to one or more of the parameters received from the user, such as to identify trends in the parameterized sensory input or to otherwise improve the efficacy of a further performance of the technique 400 for that user. In another example, the machine learning functionality can use data indicating how the user interacted with the system on which the technique 400 is performed, such as to modify future performances of the technique 400.

For example, the machine learning functionality can compare the second and third parameters received from the user and analyze the results of the comparison against the particular operation of the GUI. The machine learning functionality can then adjust how the GUI is operated during a future performance of the technique 400. For example, a future performance of the technique 400 can use the machine learning functionality output to change the manner in which elements traverse a display of the system, a speed at which the elements traverse the display, or the like.

In some implementations, a device for measuring brain activity may be used in connection with the performance of the technique 400. For example, an electroencephalography (EEG) device may be worn by a user of the software program. The EEG device may use sensors to measure the electrical activity of the brain of the user during the running of the software program. For example, the second and third parameters may represent automated measurements taken by the EEG device at respective times during the performance of the technique 400. In some implementations, such as where the software program includes a virtual reality aspect, the EEG device may be included in a virtual reality headset or like device used to view the GUI output as part of the software program.

In some implementations, the second and third parameters may be determined using facial recognition software. For example, a camera device can take images of the face of the user at the respective times during the performance of the technique 400. Facial recognition software can analyze the image taken as the second parameter against the image taken as the third parameter to determine whether the third parameter reflects a reduced disturbance level for the user. For example, the facial recognition software may be trained to detect user disturbance levels based on facial expressions.

Figure 5:
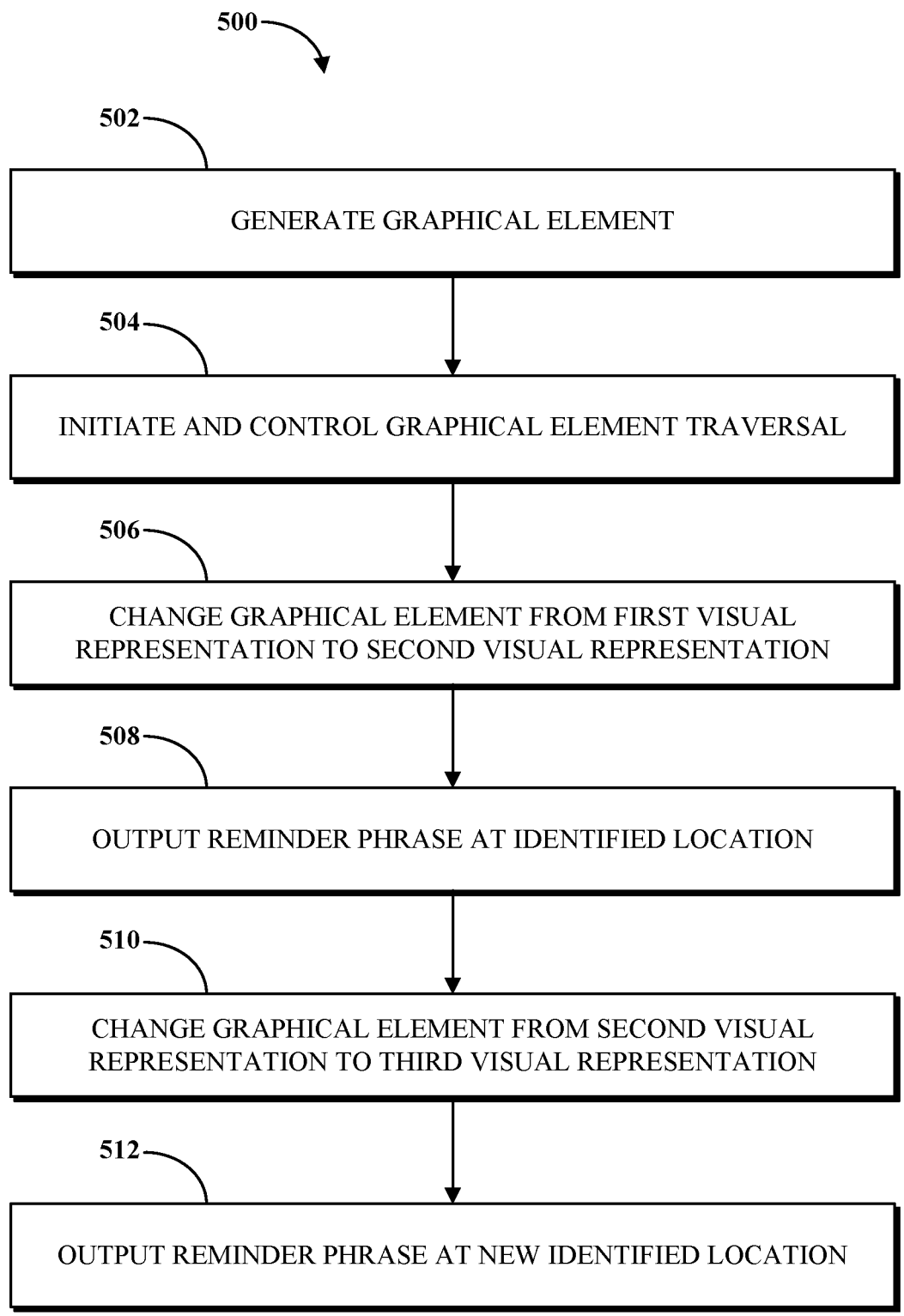
FIG. 5 is a flowchart illustrating an example of a technique for operating a GUI including a graphical element.

FIG. 5 is a flowchart illustrating an example of a technique 500 for operating a GUI including a graphical element. The technique 500 may, for example, represent or otherwise include operations performed as part of the technique 400, such as at 406 as shown in FIG. 4. At 502, a graphical element is generated. Generating the graphical element can include rendering a first visual representation of the graphical element within the GUI. For example, there may be multiple visual representations of the graphical element stored within a file used to run the software program associated with the technique 500. Rendering the first visual representation of the graphical element can include selecting one of those multiple visual representations and including it in an initial location of the GUI.

As will next be described, operating the GUI includes controlling a traversal of the graphical element across the display, controlling a change of the graphical element over time, and controlling an outputting of the reminder phrase to the display over time. At 504, the traversal of the graphical element is initiated and controlled. Initiating and controlling the traversal of the graphical element includes causing the graphical element to traverse (e.g., horizontally, vertically, or otherwise) the GUI. At 506, a visual representation of the graphical element is changed from a first visual representation to a second visual representation. At 508, a reminder phrase is output at an identified location of the GUI. Controlling the outputting of the reminder phrase to the identified location includes randomly flashing the reminder phrase at the identified location. The identified location may be a random location of the GUI, such as a location selected randomly by the software program.

Randomly flashing the reminder phrase at the identified location includes outputting the reminder phrase for display for only a fraction of a second. As such, the reminder phrase is output for display for generally too short of a period of time to be read by a user of the software program during the operation of the software program (e.g., without the user paying particular attention to the specific identified location selected for displaying the reminder phrase).

The controlling of the graphical element and outputting of the reminder phrase continue during the operation of the GUI. At 510, the visual representation of the graphical element is changed from the second visual representation to a third visual representation. That is, during the operation of the GUI, the graphical element will change, such as in visual representation, some number of times (e.g., N, where N may be a defined or random number). The changes may be related to tasks for the user of the software program to perform. For example, the tasks may include having the user interact with an input interface upon identifying that the visual representation of the graphical element has changed. At 512, the reminder phrase is output at a new identified location of the GUI. Outputting the reminder phrase to the new identified location includes randomly flashing the reminder phrase at a different part of the display than the identified location at which it was earlier flashed.

In some implementations, the operations performed at 504, 506, and 508 may be arranged in a sequence other than as shown in FIG. 5. For example, the operations performed at 506 or 508 may be performed earlier than the operations performed at 504. In another example, the operations performed at two or more of 504, 506, or 508 may be concurrently performed. In yet another example, the operations performed at 512 may be performed earlier than the operations performed at 510. In yet another example, the operations performed at 510 and 512 may be concurrently performed.

In some implementations, the timing of aspects of the technique 500 may be randomized. As such, the operations performed at certain steps of the technique 500 may be performed multiple times before operations at a subsequent step thereof are performed. For example, the reminder phrase may randomly flash multiple times before the visual representation of the graphical element changes once. In another example, the graphical element may change between multiple visual representations before the reminder phrase is randomly flashed once. These examples are provided for description and do not limit other possible examples.

While this disclosure has been described in connection with certain implementations, it is to be understood that this disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An apparatus, comprising:
an input interface;
a memory; and
a processor configured to execute instructions stored in the memory to:
control a traversal of a graphical element on a graphical user interface;
while the graphical element is controlled to traverse the graphical user interface, repeatedly perform instructions to:
obtain a random time at which a stimulus is to be output;
obtain a random duration associated with the stimulus;
output, for a user, the stimulus at the random time and for the random duration, wherein the random duration is such that the output of the stimulus is outside a conscious awareness of the user, and wherein the output of the stimulus is configured to decrease a disturbance level associated with a disturbing memory of the user; and
monitor a performance of a task related to the graphical element; and
determine a score associated with the user based on the performance of the task.

2. The apparatus of claim 1, wherein the instructions to monitor the performance of the task related to the graphical element comprises instructions to:
receive and process an input indicative of user interaction with the input interface by the user while the graphical element is controlled to traverse the graphical user interface.

3. The apparatus of claim 2, wherein the instructions to receive and process the input include instructions to:
correlate the input with changes to the graphical element while the graphical element is controlled to traverse the graphical user interface.

4. The apparatus of claim 3, wherein the instructions to correlate the input with the changes to the graphical element while the graphical element is controlled to traverse the graphical user interface include instructions to:
 score the input based on a time interval between a first time at which the graphical element is changed and a second time at which the input is received.

5. The apparatus of claim 1, wherein the graphical element is controlled to traverse across a display of the apparatus.

6. The apparatus of claim 5, wherein the instructions to control the traversal of the graphical element across the display comprise instructions to:
 cause the graphical element to traverse the graphical user interface in at least one of a horizontal direction, a vertical direction, or a diagonal direction.

7. The apparatus of claim 5, wherein the instructions to monitor the performance of the task related to the graphical element comprises instructions to:
 control a change of the graphical element over time.

8. The apparatus of claim 7, wherein the instructions to control the change of the graphical element over time include instructions to:
 cause the change of the graphical element from a first representation to a second representation.

9. The apparatus of claim 1, wherein the stimulus is a reminder phrase, and wherein the instructions to output, for the user, the stimulus at the random time and for the random duration comprises instructions to:
 cause the reminder phrase to randomly flash at one or more locations of the graphical user interface.

10. The apparatus of claim 9, wherein the one or more locations of the graphical user interface are selected according to a defined list of possible locations for the reminder phrase.

11. The apparatus of claim 9, wherein the disturbing memory is associated with the stimulus.

12. The apparatus of claim 11, wherein the instructions further comprise instructions to:
 receive, from the user, a rating of the disturbance level associated with the disturbing memory.

13. A system, comprising:
 a server device including a memory and a processor, wherein the processor executes instructions stored in the memory to:
  control a traversal of a graphical element across a graphical user interface;
  while the graphical element is controlled to traverse the graphical user interface, repeatedly perform instructions to:
   obtain a random time at which a stimulus is to be output;
   obtain a random duration associated with the stimulus;
   output, for a user, the stimulus at the random time and for the random duration, wherein the random duration is less than a duration required by the user to process the stimulus, and wherein the output of the stimulus is configured to decrease a disturbance level associated with a disturbing memory of the user; and
   monitor a performance of a task related to the graphical element; and
  determine a score associated with the user based on the performance of the task.

14. The system of claim 13, wherein the stimulus is a reminder phrase that is output on the graphical user interface.

15. The system of claim 13, wherein the stimulus is an audial stimulus.

16. The system of claim 13, the instructions to control the traversal of the graphical element across the graphical user interface comprise instructions to:
 cause the graphical element to traverse the graphical user interface in at least one of a horizontal direction, a vertical direction, or a diagonal direction.

17. A method, comprising:
 controlling a traversal of a graphical element across a graphical user interface;
 while the graphical element is controlled to traverse the graphical user interface, repeatedly performing:
  obtaining a random time at which a stimulus is to be output;
  obtaining a random duration associated with the stimulus;
  outputting, for a user, the stimulus at the random time and for the random duration, wherein the random duration is less than a duration required by the user to process the stimulus; and
  monitoring a performance of a task related to the graphical element; and
 determining a score associated with the user based on the performance of the task.

18. The method of claim 17, wherein the stimulus is a reminder phrase that is output on the graphical user interface.

19. The method of claim 17, wherein the stimulus is an audial stimulus.

20. The method of claim 17, wherein controlling the traversal of the graphical element across the graphical user interface comprises:
 modifying a location of the graphical element on the graphical user interface in at least one of a horizontal direction, a vertical direction, or a diagonal direction.

* * * * *